United States Patent
Hartmann et al.

(10) Patent No.: US 12,410,118 B2
(45) Date of Patent: Sep. 9, 2025

(54) GLYCEROL (METH)ACRYLATE CARBOXYLIC ESTER HAVING A LONG SHELF LIFE

(71) Applicant: Evonik Operations GmbH, Essen (DE)

(72) Inventors: Patrik Hartmann, Buettelborn (DE); Marita Kaufmann, Griesheim (DE); Steffen Krill, Mühltal (DE); Thorben Schütz, Alsbach-Hähnlein (DE); Marcel Treskow, Darmstadt (DE); Andrea Wittkowski, Gross-Umstadt (DE)

(73) Assignee: Evonik Operations GmbH, Essen (DE)

( * ) Notice: Subject to any disclaimer, the term of this patent is extended or adjusted under 35 U.S.C. 154(b) by 295 days.

(21) Appl. No.: 17/750,383

(22) Filed: May 22, 2022

(65) Prior Publication Data

US 2022/0281801 A1    Sep. 8, 2022

Related U.S. Application Data

(62) Division of application No. 16/479,497, filed as application No. PCT/EP2017/079124 on Nov. 14, 2017, now Pat. No. 11,414,373.

(30) Foreign Application Priority Data

Jan. 20, 2017 (EP) ..................... 17152399

(51) Int. Cl.
C07C 69/732        (2006.01)

(52) U.S. Cl.
CPC ................. C07C 69/732 (2013.01)

(58) Field of Classification Search
None
See application file for complete search history.

(56) References Cited

U.S. PATENT DOCUMENTS

| | | | |
|---|---|---|---|
| 4,458,007 A | 7/1984 | Geissler et al. |
| 4,540,743 A | 9/1985 | Schulz et al. |
| 5,080,998 A | 1/1992 | Irving |
| 6,281,271 B1 | 8/2001 | Rumphorst et al. |
| 6,384,238 B1 | 5/2002 | Zicar |
| 7,659,425 B2 | 2/2010 | Weikard et al. |
| 11,319,276 B2 | 5/2022 | Treskow et al. |
| 11,414,373 B2 | 8/2022 | Hartmann et al. |
| 2005/0250923 A1 | 11/2005 | Palmese et al. |
| 2006/0173213 A1 | 8/2006 | Chen |
| 2009/0001322 A1 | 1/2009 | Wiesler et al. |
| 2012/0219885 A1 | 8/2012 | Fäcke et al. |
| 2013/0022914 A1 | 1/2013 | Tanaka et al. |
| 2015/0232409 A1 | 8/2015 | Misske et al. |
| 2016/0229863 A1 | 8/2016 | Hillmyer et al. |
| 2016/0289160 A1 | 10/2016 | Oba et al. |
| 2017/0022142 A1 | 1/2017 | Knebel et al. |
| 2017/0088502 A1 | 3/2017 | Goto et al. |
| 2020/0331845 A1 | 10/2020 | Treskow et al. |
| 2021/0163439 A1 | 6/2021 | Treskow et al. |
| 2021/0179529 A1 | 6/2021 | Treskow et al. |
| 2021/0179531 A1 | 6/2021 | Treskow et al. |
| 2021/0214297 A1 | 7/2021 | Bleith et al. |
| 2021/0269393 A1 | 9/2021 | Treskow et al. |
| 2021/0332005 A1 | 10/2021 | Treskow et al. |
| 2022/0056005 A9 | 2/2022 | Treskow et al. |
| 2022/0112154 A1 | 4/2022 | Treskow et al. |
| 2022/0281798 A1 | 9/2022 | Treskow et al. |

FOREIGN PATENT DOCUMENTS

| | | |
|---|---|---|
| CS | 200 395 | 9/1980 |
| EP | 2 899 214 | 7/2015 |
| EP | 3 235 801 | 10/2017 |
| EP | 3248959 | 11/2017 |
| FR | 2 739 850 | 4/1997 |
| JP | S58-131940 | 8/1983 |
| JP | H05-98031 | 4/1993 |
| JP | H06-199962 | 7/1994 |
| JP | H06-287241 | 10/1994 |
| JP | H07-330847 | 12/1995 |
| JP | H10-226692 | 8/1998 |
| JP | H10-265312 | 10/1998 |
| JP | 2002-088018 | 3/2002 |
| JP | 2003-176318 | 6/2003 |
| JP | 2007 091665 | 4/2007 |
| JP | 2014-098100 | 5/2014 |
| JP | 2014-111550 | 6/2014 |
| JP | 2014148386 | 8/2014 |
| JP | 2015186787 | 10/2015 |
| KR | 10-1855122 | 6/2018 |
| WO | WO 00/59982 | 10/2000 |
| WO | WO 2004/007418 | 1/2004 |

(Continued)

OTHER PUBLICATIONS

Die Angewandte Makromolekulare Chemie 90 (1980) 47-55.*
Labsky et al., Die Angewandte Makromolekulare Chemie, year 1980, p. 47-55.*
U.S. Appl. No. 17/750,273, filed May 20, 2022, US-2022/0281798 A1, Sep. 8, 2022, Treskow.
Clark, et al., "A One-Step Procedure for the Monoacylation of Symmetrical 1,2-Diols," *J. Org. Chem.* 67:5226-5231 (2002).
English language translation of the International Search Report for corresponding PCT/EP2017/079124, filed Nov. 14, 2017.
English language translation of the Written Opinion of the International Searching Authority for corresponding PCT/EP2017/079124, filed Nov. 14, 2017.
English language translation of the International Preliminary Report on Patentability for corresponding PCT/EP2017/079124, filed Nov. 14, 2017.

(Continued)

*Primary Examiner* — Ana Z Muresan
(74) *Attorney, Agent, or Firm* — Law Office of Michael A. Sanzo, LLC

(57) ABSTRACT

The present invention is to storage-stable compositions containing glycerol (meth)acrylate carboxylic esters, carboxylic acids and, optionally, Broensted acids.

16 Claims, No Drawings

(56) References Cited

FOREIGN PATENT DOCUMENTS

WO    WO 2005/090281    9/2005
WO    WO 2018/031373    2/2018

OTHER PUBLICATIONS

European Search Report and Opinion for corresponding EP 17 15 2399, filed Jan. 20, 2017, with partial English language machine translation of the Search Opinion attached.
Ishihara, et al., "Scandium Trifluoromethanesulfonate as an Extremely Active Acylation Catalyst," *J. Am. Chem. Soc.* 117:4413-4414 (1995).
Pansare, et al., "Magnesium Bromide Catalysed Acylation of Alcohols," *Synethetic Comm.* 30(14):2587-2592 (2000).
Yoshinori Nakane, et al., "New crosslinking system using blocked carboxylic acid," Progress in Organic Coating 31:113-120 (1997).
U.S. Appl. No. 16/973,995, filed Dec. 10, 2020, US-2021/0163439 A1, Jun. 3, 2021, Treskow.
U.S. Appl. No. 17/057,659, filed Nov. 21, 2020, US-2021/0214297 A1, Jul. 15, 2021, Bleith.
U.S. Appl. No. 17/260,223, filed Jan. 14, 2021, US-2021/0332005 A1, Oct. 28, 2021, Treskow.
U.S. Appl. No. 17/260,226, filed Jan. 14, 2021, US-2021/0269393 A1, Sep. 2, 2021, Treskow.
U.S. Appl. No. 17/262,735, filed Jan. 24, 2021, US-2022/0112154 A1, Apr. 14, 2022, Treskow.
U.S. Appl. No. 17/268,463, filed Feb. 13, 2021, US-2021/0179529 A1, Jun. 17, 2021, Treskow.
Kubala, "Magnesium Oxide: Benefits, Side Effects, Dosage, and Interactions," Nutrition, 15 pages, published 2021 (copending U.S. Appl. No. 17/268,463).
Patil, et al., "Chemoselective Acylation of Amines, Alcohols and Phenols Using Magnesium Chloride Under Solvent Free Condition," *Int. J. Chem. Sci.* 13(1):450-458 (2015).

\* cited by examiner

GLYCEROL (METH)ACRYLATE CARBOXYLIC ESTER HAVING A LONG SHELF LIFE

CROSS REFERENCE TO RELATED APPLICATIONS

The present application is a division of U.S. Ser. No. 16/479,497, which is US national stage of international application PCT/EP2017/079124, which had an international filing date of Nov. 14, 2017, and which was published on Jul. 26, 2018. The PCT application claims priority to EP 17152399.6, filed on Jan. 20, 2017.

The present invention describes storage-stable glycerol (meth)acrylate carboxylic esters and a method for preparing these esters.

Methods for preparing glycerol (meth)acrylate carboxylic esters are known from the prior art.

Glycerol dimethacrylate is prepared from glycidyl methacrylate and methacrylic acid in the presence of catalytic amounts of a quaternary ammonium salt (in the specific case this is benzyltriethylammonium chloride).

The prior art describes methods for preparing glycerol dimethacrylate from methacrylic acid and glycidyl methacrylate in the presence of catalysts. It is preferable to use quaternary ammonium salts as catalysts.

<2 percent of unconverted glycidyl methacrylate remain in the product mixture in this reaction. It is known that glycidyl methacrylate exhibits genotoxicity in in vitro tests (OECD SIDS report "Glycidyl methacrylate", 2000).

EP 0054700 describes a method for preparing glycerol dimethacrylate. Here, glycidyl methacrylate is added to a mixture of methacrylic acid, benzyltriethylammonium chloride and p-methoxyphenol at a temperature of 80° C. After work-up with sodium carbonate solution, phase separation and drying, the mixture is subjected to a fractional distillation. The yield is only 75%. In addition, the product polymerizes as a result of the purification by distillation. The distillation can therefore only be carried out with small amounts which is not economically viable for an industrial scale reaction.

WO2015/124458 discloses a process for preparing high-purity glycerol dimethacrylate. It describes the use of an acidic adsorbent for the post-treatment (purification) of a glycidyl methacrylate-containing glycerol dimethacrylate which was prepared in accordance with EP 0054700.

EP 1693359 describes the preparation of hydroxyalkyl (meth)acrylates. In this case, epoxide group-containing compounds are reacted with carboxylic acids in the presence of Lewis acids which each bear at least one directly bound di(cyclo)alkylamino group. The examples show that the product was found in the GPC up to at most 80 area %. An additional method step is also described which is intended to bring the epoxide content below 0.2% by weight. The Lewis acids used are uninteresting for industrial scale reactions since they are obtainable on the world market only in small amounts at high prices.

CS 200395 describes a method for preparing a monomer mixture by reacting (meth)acrylic acid with glycidyl (meth)acrylate in the presence of hydroquinone and triethylamine. The subsequent multi-stage purification includes an extraction with an aqueous alkali metal carbonate solution and subsequent extraction with an aqueous sulfuric acid and finally an extraction with water.

WO2005090281 describes a dental material comprising a (meth)acrylic acid and compounds with salicylic acid structure which are crosslinked with di-, tri- or higher valent compounds. 4-Hydroxysalicylic acid is reacted with sodium hydroxide and glycidyl methacrylate. The para-linked addition product of 4-hydroxysalicylic acid and glycidyl methacrylate is formed at only 20% yield.

WO0059982 describes a method for preparing highly crosslinked polyesters in which polycarboxylic acid anhydride is reacted with a polyol in the presence of an amine and the resulting acid is reacted with glycidyl (meth)acrylate or allyl glycidyl ether. This product is subsequently reacted with an anhydride.

EP951896 describes a method for preparing two-component and multi-component free-radically polymerizable dental materials. After the reaction of acrylic acid, mercaptoethanol and a radical initiator, half of the oligocarboxylic acid obtained is further reacted directly with glycidyl methacrylate. On account of the large excess of acid, there is no disproportionation.

On storage of glycerol dimethacrylate, disproportionation of the product may occur. In this case, glycerol monomethacrylate and glycerol trimethacrylate are formed.

It was an object to provide storage-stable glycerol (meth)acrylate carboxylic esters and a method for preparing storage-stable glycerol (meth)acrylate carboxylic esters.

The object was achieved by storage-stable glycerol (meth)acrylate carboxylic esters of the formula (I)

Formula (I)

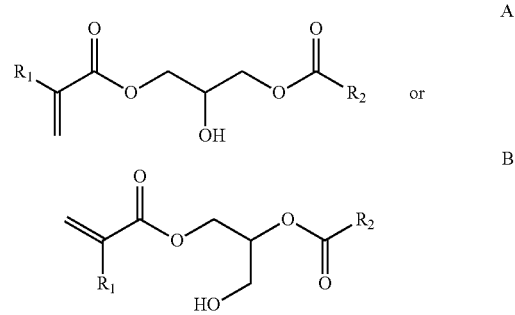

where
$R_1$=H or $CH_3$,
$R_2$=hydrogen, or aliphatic carbons with C1 to C30, or aliphatic cyclic carbon compounds having a ring size of C4 to C8, unsubstituted or substituted by N, S, O or P, or halogenated aliphatic carbon compounds with C1 to C8, or aromatic carbon compounds, or heteroaromatic carbon compounds substituted by N, S, O or P, or unsaturated aliphatic carbon compounds with C2 to C30 characterized in that carboxylic acids of the formula (II) endogenous to the system Formula (II)

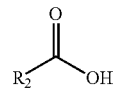

where
$R_2$=hydrogen, or aliphatic carbons with C1 to C30, or aliphatic cyclic carbon compounds having a ring size of C4 to C8, unsubstituted or substituted by N, S, O or P, or halogenated aliphatic carbon compounds with C1 to C8, or aromatic carbon compounds, or heteroaromatic carbon compounds substituted by N, S, O or P, or unsaturated aliphatic carbon compounds with C2 to C30 and optionally carboxylic acids of the formula (III)

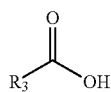

Formula (III)

where

R$_3$=hydrogen, or aliphatic carbons with C1 to C30, or aliphatic cyclic carbon compounds having a ring size of C4 to C8, unsubstituted or substituted by N, S, O or P, or halogenated aliphatic carbon compounds with C1 to C8, or aromatic carbon compounds, or heteroaromatic carbon compounds substituted by N, S, O or P, or unsaturated aliphatic carbon compounds with C2 to C30, individually or in mixtures and optionally any further Broensted acids foreign to the system are present in sum total at a molar excess to the glycidyl (meth)acrylate present.

The term acids in accordance with the invention includes both carboxylic acids of the formula (II) endogenous to the system and carboxylic acids of the formula (III) and mixtures thereof, but also Broensted acids foreign to the system. Carboxylic acids (II) endogenous to the system include carboxylic acids which react with glycidyl (meth)acrylate to give the glycerol (meth)acrylate carboxylic esters (I).

The molar excess of the sum total of the acids in the storage-stable glycerol (meth)acrylate carboxylic esters includes both the presence of the carboxylic acids (II) endogenous to the system alone in excess, and any desired acid mixtures.

For example, a carboxylic acid or mixtures of different carboxylic acids according to formula (III) may be present in sum total in molar excess. A further alternative provides any Broensted acids alone or in mixtures, but also in mixtures with carboxylic acids of the formula (II) endogenous to the system and/or carboxylic acids of the formula (III) and mixtures thereof.

The molar excess of the acids in sum total in accordance with the invention is in a molar ratio of the acids to the glycidyl (meth)acrylate present of from 1.001:1 to 5:1.

Preference is given to storage-stable glycerol (meth)acrylate carboxylic esters having a molar ratio of acid to glycidyl (meth)acrylate in a ratio of from 1.01:1 to 2:1, particularly preferably in a ratio of from 1.02:1 to 1.5:1.

The ratio in accordance with the invention of acid to glycidyl (meth)acrylate is preferably present at the end of the addition of the reactants carboxylic acid (II) endogenous to the system and glycidyl (meth)acrylate.

Alternatively, this ratio is present also after the synthesis, i.e. prior to storage.

It has been shown that, prior to storage, the ratio can be adjusted by the addition of both the carboxylic acid according to formula (II) endogenous to the system and with carboxylic acids of the formula (III) foreign to the system or inorganic Broensted acids foreign to the system.

Particular preference is given to a storage-stable glycerol (meth)acrylate carboxylic ester characterized in that the carboxylic acid endogenous to the system is a (meth)acrylic acid with a molar ratio of (meth)acrylic acid to glycidyl (meth)acrylate of from 1.01:1 to 2:1.

The object was also achieved by providing a method for preparing storage-stable glycerol (meth)acrylate carboxylic esters. The method in accordance with the invention is characterized in that carboxylic acids of the formula (II) endogenous to the system

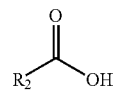

Formula (II)

where

R$_2$=hydrogen, or aliphatic carbons with C1 to C30, or aliphatic cyclic carbon compounds having a ring size of C4 to C8, unsubstituted or substituted by N, S, O or P, or halogenated aliphatic carbon compounds with C1 to C8, or aromatic carbon compounds, or heteroaromatic carbon compounds substituted by N, S, O or P, or unsaturated aliphatic carbon compounds with C2 to C30 and glycidyl (meth)acrylate are reacted at temperatures of 20-130° C. in the presence of a catalyst, by initially charging carboxylic acid (II) endogenous to the system and adding glycidyl (meth)acrylate continuously, and optionally adding carboxylic acids of the formula (III)

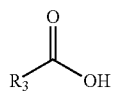

Formula (III)

where

R$_3$=hydrogen, or aliphatic carbons with C1 to C30, or aliphatic cyclic carbon compounds having a ring size of C4 to C8, unsubstituted or substituted by N, S, O or P, or halogenated aliphatic carbon compounds with C1 to C8, or aromatic carbon compounds, or heteroaromatic carbon compounds substituted by N, S, O or P, or unsaturated aliphatic carbon compounds with C2 to C30, individually or in mixtures and/or optionally adding any further Broensted acids foreign to the system in sum total at a molar excess to the glycidyl (meth)acrylate present.

It has been found that a distinctly improved storage stability can be achieved by suppressing the disproportionation by targeted adjustment of the ratio of the residual contents of acid and glycidyl (meth)acrylate in the end product.

A product is storage-stable for the time in which it is still able to maintain the specified product specification after storage at 30° C. or higher. This is defined by the content of disproportionation products not exceeding a maximum value when stored at specified temperatures, for example at 30° C. or 50° C. At the same time, diesters must not fall below a minimum value. Storage periods of 1 month, 3 months, 6 months and 8 months are defined.

Glycerol (meth)acrylate carboxylic esters are storage-stable in accordance with the invention if the threshold value does not fall below 85% by weight for diesters or exceed 3% by weight for triesters. It has been found, surprisingly, that with an excess of acid, the glycerol (meth)acrylate carboxylic esters are always storage-stable at 30° C. over the course of 8 months. If the storage is at 50° C., a storage stability of at least 3 months, preferably more than 6 months, especially preferably more than 8 months, can be achieved.

The molar ratio of acid to glycidyl (meth)acrylate may be adjusted to a ratio of from 1.001:1 to 5:1 by using appropriate amounts of carboxylic acids endogenous to the system. The molar ratio of carboxylic acid to glycidyl (meth)acrylate is preferably adjusted to a ratio of from 1.01:1 to 2:1, particularly preferably of from 1.02:1 to 1.5:1. These molar ratios are present in accordance with the invention at the end of the addition of the reactants.

It has been found, surprisingly, that independently of the molar ratio of carboxylic acid to glycidyl (meth)acrylate at the end of the addition of the reactants, a storage-stable glycerol (meth)acrylate carboxylic ester can be prepared by adjusting to a molar ratio of from 1.001:1 to 5:1 by addition of acids after the synthesis, in particular before storage. The molar ratio of acid to glycidyl (meth)acrylate is preferably adjusted to a ratio before storage of from 1.01:1 to 2:1, particularly preferably of from 1.02:1 to 1.5:1, optionally by addition of an acid.

It has been found that carboxylic acids endogenous to the system are suitable, but also carboxylic acids foreign to the system and Broensted acids foreign to the system may be added in order to set the required molar ratio of acid to glycidyl (meth)acrylate.

The molar content of acid in the end product must be greater than the molar content of glycidyl (meth)acrylate during storage.

The glycerol (meth)acrylate carboxylic ester is present as an isomeric mixture. The isomeric ratio is dependent on the reaction conditions. The epoxide ring opening shifts as a function of the reaction temperature and therefore influences the distribution of the isomers A and B of formula (I).

The reactants used are carboxylic acids of the formula (II).

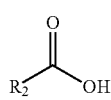

Formula (II)

where
$R_1$=H or $CH_3$,
$R_2$=hydrogen, or aliphatic carbons with C1 to C30, or aliphatic cyclic carbon compounds having a ring size of C4 to C8, unsubstituted or substituted by N, S, O or P, or halogenated aliphatic carbon compounds with C1 to C8, or aromatic carbon compounds, or heteroaromatic carbon compounds substituted by N, S, O or P, or unsaturated aliphatic carbon compounds with C2 to C30.

The carboxylic acids of the formula (II) also include functionalized aliphatic carboxylic acids with functional groups selected from the group comprising hydroxides, nitriles, esters, amides, ketones, thiols and ethers.

Carboxylic acids from the following groups are suitable: hydroxycarboxylic acids, saturated carboxylic acids, unsaturated and polyunsaturated carboxylic acids, aromatic carboxylic acids, cyclic and heterocyclic carboxylic acids, heteroaromatic carboxylic acids and halogenated carboxylic acids.

Particular preference is given to carboxylic acids selected from the group comprising hydroxyisobutyric acid (HIBA), methacrylic acid, acrylic acid, acetic acid, butyric acid, stearic acid, benzoic acid, salicylic acid, nicotinic acid, proline, oleic acid, lactic acid and trichloroacetic acid.

The carboxylic acids are reacted with glycidyl (meth)acrylate. This notation signifies both glycidyl methacrylate and glycidyl acrylate.

The method is conducted at temperatures between 20 and 130° C., preferably at temperatures between 85 and 110° C.

At temperatures over 130° C., the acute risk of polymerization exists. Therefore, the carboxylic acid is preferably initially charged and the glycidyl (meth)acrylate is metered in such that the reaction temperature remains within the specified limits.

Carboxylic acids having melting points above the reaction temperature require the use of high-boiling solvents inert under the reaction conditions. Suitable solvents are toluene, dimethylformamide, nitrobenzene, dibutyl ether, chlorobenzene and further solvents from the group of high-boiling solvents.

The reaction is effected preferably in the presence of a catalyst.

Suitable catalysts are quaternary alkylammonium halides, triphenylphosphine, triphenylphosphine oxide, hexamethylenetetramine, tetramethylammonium bromide, tetrabutylammonium bromide, N,N-dimethylbenzylamine and active Cr(III) complexes.

Particular preference is given to using benzyltriethylammonium chloride, benzyltriethylammonium bromide, tetrabutylammonium chloride or tetrabutylammonium bromide.

EXAMPLES

The carboxylic acid, 0.05 g of hydroquinone monomethyl ether and 9.60 g of benzyltriethylammonium chloride as catalyst were initially charged and heated to 90° C. in a 1 l Witt's flask with oil circulation, bottom outlet valve, porcelain blade stirrer with stirrer motor, 500 ml addition funnel as well as a thermometer and air inlet. At 90-91° C., 300 g of glycidyl (meth)acrylate are added over a period of 60 minutes. At the end of the addition, the mixture is heated to 97° C., the temperature briefly increasing here to a maximum of 100° C. The mixture is maintained at 97° C. for 10 h, then cooled and discharged. From the product thus obtained, storage stability tests were carried out at 30 and 50° C. in order to establish the tendency of the product toward disproportionation.

Preparation Example 1

Method is distinguished in that 179 g of methacrylic acid is used as carboxylic acid.
Molar Stoichiometry (Glycidyl Methacrylate:Carboxylic Acid) 1:0.985

| Storage stability at 30° C. | Start | 1 month | 3 months | 6 months | 8 months |
|---|---|---|---|---|---|
| Diester content [%] | min. 85.00 | 86.1% | 81.7% | 53.0% | 48.7% | 48.4% |
| Triester content [%] | max. 3.00 | 1.6% | 5.4% | 28.1% | 33.3% | 33.7% |

-continued

| Storage stability at 30° C. | Start | 1 month | 3 months | 6 months | 8 months |
|---|---|---|---|---|---|
| Methacrylic acid [%] | 0.40% | n.d. | n.d. | n.d. | n.d. |
| Glycidyl methacrylate [%] | 0.78% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 86.1% | 49.0% | 46.8% | 47.2% | 47.0% |
| Triester content [%] | max. 3.00 | 1.6% | 31.9% | 33.6% | 33.8% | 33.6% |
| Methacrylic acid [%] | | 0.40% | n.d. | n.d. | n.d. | n.d. |
| Glycidyl methacrylate [%] | | 0.78% | n.d. | n.d. | n.d. | n.d. |

Conclusion: The product prepared with a molar stoichiometry of 1:0.985 at the end of the reactant addition proved to be NOT storage-stable!

Preparation Example 2

Molar Stoichiometry (Glycidyl Methacrylate:Carboxylic Acid) 1:1

Method is distinguished in that the procedure is carried out analogously to Example 1 but 181.7 g of methacrylic acid is used as carboxylic acid.

| Storage stability at 30° C. | | Start | 1 month | 3 months | 6 months | 8 months |
|---|---|---|---|---|---|---|
| Diester content [%] | min. 85.00 | 86.2% | 81.8% | 53.1% | 48.8% | 48.5% |
| Triester content [%] | max. 3.00 | 1.8% | 6.1% | 31.5% | 37.4% | 37.8% |
| Methacrylic acid [%] | | 0.42% | n.d. | n.d. | n.d. | n.d. |
| Glycidyl methacrylate [%] | | 0.72% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 86.2% | 49.1% | 46.9% | 47.2% | 47.1% |
| Triester content [%] | max. 3.00 | 1.8% | 35.8% | 37.7% | 37.9% | 37.6% |
| Methacrylic acid [%] | | 0.42% | n.d. | n.d. | n.d. | n.d. |
| Glycidyl methacrylate [%] | | 0.72% | n.d. | n.d. | n.d. | n.d. |

Conclusion: The product prepared with a molar stoichiometry of 1:1 at the end of the reactant addition proved to be NOT storage-stable!

Inventive Example 3

Molar Stoichiometry (Glycidyl Methacrylate:Carboxylic Acid) 1:1.02

Method is distinguished in that the procedure is carried out analogously to Example 1 but 185.3 g of methacrylic acid is used as carboxylic acid.

| Storage stability at 30° C. | | Start | 1 month | 3 months | 6 months | 8 months |
|---|---|---|---|---|---|---|
| Diester content [%] | min. 85.00 | 89.3% | 90.0% | 89.8% | 89.9% | 89.3% |
| Triester content [%] | max. 3.00 | 1.5% | 1.5% | 1.5% | 1.6% | 1.9% |
| Methacrylic acid [%] | | 0.45% | n.d. | n.d. | n.d. | n.d. |
| Glycidyl methacrylate [%] | | 0.65% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 89.3% | 89.4% | 89.3% | 88.7% | 87.2% |
| Triester content [%] | max. 3.00 | 1.5% | 1.7% | 2.0% | 2.6% | 3.0% |
| Methacrylic acid [%] | | 0.45% | n.d. | n.d. | n.d. | n.d. |
| Glycidyl methacrylate [%] | | 0.65% | n.d. | n.d. | n.d. | n.d. |

Conclusion: The product prepared with a molar stoichiometry of 1:1.02 at the end of the reactant addition had a storage stability of more than 8 months.

Preparation Example 4

Method is distinguished in that the procedure is carried out analogously to Example 1 but 124.8 g of acetic acid is used as carboxylic acid.
Molar Stoichiometry (Glycidyl Methacrylate:Carboxylic Acid) 1:0.985

| Storage stability at 30° C. | | Start | 1 month | 3 months | 6 months | 8 months |
|---|---|---|---|---|---|---|
| Diester content [%] | min. 85.00 | 86.8% | 82.4% | 53.5% | 49.1% | 48.8% |
| Triester content [%] | max. 3.00 | 1.7% | 5.8% | 29.7% | 35.3% | 35.7% |
| Acetic acid [%] | | 0.31% | n.d. | n.d. | n.d. | n.d. |
| Glycidyl methacrylate [%] | | 0.88% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 86.8% | 49.5% | 47.3% | 47.6% | 47.4% |
| Triester content [%] | max. 3.00 | 1.7% | 33.8% | 35.6% | 35.8% | 35.5% |
| Acetic acid [%] | | 0.31% | n.d. | n.d. | n.d. | n.d. |
| Glycidyl methacrylate [%] | | 0.88% | n.d. | n.d. | n.d. | n.d. |

Conclusion: The product prepared with a molar stoichiometry of 1:0.985 at the end of the reactant addition proved to be NOT storage-stable!

Preparation Example 5

Molar Stoichiometry (Glycidyl Methacrylate:Carboxylic Acid) 1:1
Method is distinguished in that the procedure is carried out analogously to Example 1 but 126.7 g of acetic acid is used as carboxylic acid.

| Storage stability at 30° C. | | Start | 1 month | 3 months | 6 months | 8 months |
|---|---|---|---|---|---|---|
| Diester content [%] | min. 85.00 | 87.0% | 82.5% | 53.6% | 49.2% | 48.9% |
| Triester content [%] | max. 3.00 | 1.8% | 6.1% | 31.3% | 37.2% | 37.6% |
| Acetic acid [%] | | 0.33% | n.d. | n.d. | n.d. | n.d. |
| Glycidyl methacrylate [%] | | 0.81% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 87.0% | 49.6% | 47.3% | 47.7% | 47.5% |
| Triester content [%] | max. 3.00 | 1.8% | 35.7% | 37.5% | 37.7% | 37.5% |
| Acetic acid [%] | | 0.33% | n.d. | n.d. | n.d. | n.d. |
| Glycidyl methacrylate [%] | | 0.81% | n.d. | n.d. | n.d. | n.d. |

Conclusion: The product prepared with a molar stoichiometry of 1:1 at the end of the reactant addition proved to be NOT storage-stable!

Inventive Example 6

Molar Stoichiometry (Glycidyl Methacrylate:Carboxylic Acid) 1:1.02

Method is distinguished in that the procedure is carried out analogously to Example 1 but 129.3 g of acetic acid is used as carboxylic acid.

| Storage stability at 30° C. | | Start | 1 month | 3 months | 6 months | 8 months |
|---|---|---|---|---|---|---|
| Diester content [%] | min. 85.00 | 89.4% | 90.1% | 89.9% | 90.0% | 89.3% |
| Triester content [%] | max. 3.00 | 1.7% | 1.8% | 1.7% | 1.9% | 2.2% |
| Acetic acid [%] | | 0.35% | n.d. | n.d. | n.d. | n.d. |
| Glycidyl methacrylate [%] | | 0.73% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 89.4% | 89.5% | 89.4% | 88.8% | 87.3% |
| Triester content [%] | max. 3.00 | 1.7% | 2.1% | 2.4% | 3.0% | 3.5% |
| Acetic acid [%] | | 0.35% | n.d. | n.d. | n.d. | n.d. |
| Glycidyl methacrylate [%] | | 0.73% | n.d. | n.d. | n.d. | n.d. |

Conclusion: The product prepared with a molar stoichiometry of 1:1.02 at the end of the reactant addition had a storage stability of more than 6 months.

Preparation Example 7

Method is distinguished in that the procedure is carried out analogously to Example 1 but 183.2 g of butyric acid is used as carboxylic acid.
Molar Stoichiometry (Glycidyl Methacrylate:Carboxylic Acid) 1:0.985

| Storage stability at 30° C. | | Start | 1 month | 3 months | 6 months | 8 months |
|---|---|---|---|---|---|---|
| Diester content [%] | min. 85.00 | 86.0% | 81.6% | 53.0% | 48.7% | 48.4% |
| Triester content [%] | max. 3.00 | 1.8% | 6.2% | 31.9% | 37.9% | 38.3% |
| Butyric acid [%] | | 0.40% | n.d. | n.d. | n.d. | n.d. |
| Glycidyl methacrylate [%] | | 0.78% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 86.0% | 49.0% | 46.8% | 47.1% | 47.0% |
| Triester content [%] | max. 3.00 | 1.8% | 36.3% | 38.2% | 38.4% | 38.1% |
| Butyric acid [%] | | 0.40% | n.d. | n.d. | n.d. | n.d. |
| Glycidyl methacrylate [%] | | 0.78% | n.d. | n.d. | n.d. | n.d. |

Conclusion: The product prepared with a molar stoichiometry of 1:0.985 at the end of the reactant addition proved to be NOT storage-stable!

Preparation Example 8

Molar Stoichiometry (Glycidyl Methacrylate:Carboxylic Acid) 1:1

Method is distinguished in that the procedure is carried out analogously to Example 1 but 186 g of butyric acid is used as carboxylic acid.

| Storage stability at 30° C. | | Start | 1 month | 3 months | 6 months | 8 months |
|---|---|---|---|---|---|---|
| Diester content [%] | min. 85.00 | 87.0% | 82.6% | 53.6% | 49.3% | 49.0% |
| Triester content [%] | max. 3.00 | 1.9% | 6.4% | 33.2% | 39.4% | 39.8% |
| Butyric acid [%] | | 0.42% | n.d. | n.d. | n.d. | n.d. |
| Glycidyl methacrylate [%] | | 0.71% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 87.0% | 49.6% | 47.4% | 47.7% | 47.5% |
| Triester content [%] | max. 3.00 | 1.9% | 37.8% | 39.7% | 39.9% | 39.7% |
| Butyric acid [%] | | 0.42% | n.d. | n.d. | n.d. | n.d. |
| Glycidyl methacrylate [%] | | 0.71% | n.d. | n.d. | n.d. | n.d. |

Conclusion: The product prepared with a molar stoichiometry of 1:1 at the end of the reactant addition proved to be NOT storage-stable!

Inventive Example 9

Molar Stoichiometry (Glycidyl Methacrylate:Carboxylic Acid) 1:1.02

Method is distinguished in that the procedure is carried out analogously to Example 1 but 189.7 g of butyric acid is used as carboxylic acid.

| Storage stability at 30° C. | | Start | 1 month | 3 months | 6 months | 8 months |
|---|---|---|---|---|---|---|
| Diester content [%] | min. 85.00 | 88.9% | 89.6% | 89.4% | 89.5% | 88.9% |
| Triester content [%] | max. 3.00 | 1.7% | 1.8% | 1.7% | 1.9% | 2.2% |
| Butyric acid [%] | | 0.46% | n.d. | n.d. | n.d. | n.d. |
| Glycidyl methacrylate [%] | | 0.64% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 88.9% | 89.1% | 88.9% | 88.4% | 86.9% |
| Triester content [%] | max. 3.00 | 1.7% | 2.0% | 2.4% | 3.0% | 3.5% |
| Butyric acid [%] | | 0.46% | n.d. | n.d. | n.d. | n.d. |
| Glycidyl methacrylate [%] | | 0.64% | n.d. | n.d. | n.d. | n.d. |

Conclusion: The product prepared with a molar stoichiometry of 1:1.02 at the end of the reactant addition had a storage stability of more than 6 months.

Preparation Example 10

Method is distinguished in that the procedure is carried out analogously to Example 1 but 591.4 g of stearic acid is used as carboxylic acid.
Molar Stoichiometry (Glycidyl Methacrylate:Carboxylic Acid) 1:0.985

| Storage stability at 30° C. | | Start | 1 month | 3 months | 6 months | 8 months |
|---|---|---|---|---|---|---|
| Diester content [%] | min. 85.00 | 87.0% | 82.5% | 53.5% | 49.2% | 48.9% |
| Triester content [%] | max. 3.00 | 1.3% | 4.2% | 21.7% | 25.8% | 26.1% |

| Storage stability at 30° C. | Start | 1 month | 3 months | 6 months | 8 months |
|---|---|---|---|---|---|
| Stearic acid [%] | 0.71% | n.d. | n.d. | n.d. | n.d. |
| Glycidyl methacrylate [%] | 0.42% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 87.0% | 49.6% | 47.3% | 47.7% | 47.5% |
| Triester content [%] | max. 3.00 | 1.3% | 24.7% | 26.0% | 26.2% | 26.0% |
| Stearic acid [%] | | 0.71% | n.d. | n.d. | n.d. | n.d. |
| Glycidyl methacrylate [%] | | 0.42% | n.d. | n.d. | n.d. | n.d. |

Conclusion: The product prepared with a molar stoichiometry of 1:0.985 at the end of the reactant addition proved to be NOT storage-stable!

Preparation Example 11

Molar Stoichiometry (Glycidyl Methacrylate:Carboxylic Acid) 1:1

Method is distinguished in that the procedure is carried out analogously to Example 1 but 600.4 g of stearic acid is used as carboxylic acid.

| Storage stability at 30° C. | | Start | 1 month | 3 months | 6 months | 8 months |
|---|---|---|---|---|---|---|
| Diester content [%] | min. 85.00 | 86.2% | 81.7% | 53.0% | 48.8% | 48.5% |
| Triester content [%] | max. 3.00 | 1.7% | 5.7% | 29.4% | 34.9% | 35.2% |
| Stearic acid [%] | | 0.74% | n.d. | n.d. | n.d. | n.d. |
| Glycidyl methacrylate [%] | | 0.39% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 86.2% | 49.1% | 46.9% | 47.2% | 47.1% |
| Triester content [%] | max. 3.00 | 1.7% | 33.4% | 35.1% | 35.3% | 35.1% |
| Stearic acid [%] | | 0.74% | n.d. | n.d. | n.d. | n.d. |
| Glycidyl methacrylate [%] | | 0.39% | n.d. | n.d. | n.d. | n.d. |

Conclusion: The product prepared with a molar stoichiometry of 1:1 at the end of the reactant addition proved to be NOT storage-stable!

Inventive Example 12

Molar Stoichiometry (Glycidyl Methacrylate:Carboxylic Acid) 1:1.02

Method is distinguished in that the procedure is carried out analogously to Example 1 but 612.4 g of stearic acid is used as carboxylic acid.

| Storage stability at 30° C. | | Start | 1 month | 3 months | 6 months | 8 months |
|---|---|---|---|---|---|---|
| Diester content [%] | min. 85.00 | 86.9% | 87.6% | 87.4% | 87.5% | 86.9% |
| Triester content [%] | max. 3.00 | 1.6% | 1.7% | 1.6% | 1.8% | 2.0% |

-continued

| Storage stability at 30° C. | Start | 1 month | 3 months | 6 months | 8 months |
|---|---|---|---|---|---|
| Stearic acid [%] | 0.79% | n.d. | n.d. | n.d. | n.d. |
| Glycidyl methacrylate [%] | 0.35% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 86.9% | 87.1% | 86.9% | 86.4% | 84.9% |
| Triester content [%] | max. 3.00 | 1.6% | 1.9% | 2.2% | 2.8% | 3.3% |
| Stearic acid [%] | | 0.79% | n.d. | n.d. | n.d. | n.d. |
| Glycidyl methacrylate [%] | | 0.35% | n.d. | n.d. | n.d. | n.d. |

Conclusion: The product prepared with a molar stoichiometry of 1:1.02 at the end of the reactant addition had a storage stability of more than 6 months.

Preparation Example 13

Method is distinguished in that the procedure is carried out analogously to Example 1 but 253.9 g of benzoic acid is used as carboxylic acid.
Molar Stoichiometry (Glycidyl Methacrylate:Carboxylic Acid) 1:0.985

| Storage stability at 30° C. | | Start | 1 month | 3 months | 6 months | 8 months |
|---|---|---|---|---|---|---|
| Diester content [%] | min. 85.00 | 86.2% | 81.8% | 53.1% | 48.8% | 48.5% |
| Triester content [%] | max. 3.00 | 1.7% | 5.8% | 30.1% | 35.7% | 36.1% |
| Benzoic acid [%] | | 0.49% | n.d. | n.d. | n.d. | n.d. |
| Glycidyl methacrylate [%] | | 0.68% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 86.2% | 49.1% | 46.9% | 47.2% | 47.1% |
| Triester content [%] | max. 3.00 | 1.7% | 34.2% | 36.0% | 36.2% | 36.0% |
| Benzoic acid [%] | | 0.49% | n.d. | n.d. | n.d. | n.d. |
| Glycidyl methacrylate [%] | | 0.68% | n.d. | n.d. | n.d. | n.d. |

Conclusion: The product prepared with a molar stoichiometry of 1:0.985 at the end of the reactant addition proved to be NOT storage-stable!

Preparation Example 14

Molar Stoichiometry (Glycidyl Methacrylate:Carboxylic Acid) 1:1
Method is distinguished in that the procedure is carried out analogously to Example 1 but 257.7 g of benzoic acid is used as carboxylic acid.

| Storage stability at 30° C. | | Start | 1 month | 3 months | 6 months | 8 months |
|---|---|---|---|---|---|---|
| Diester content [%] | min. 85.00 | 88.1% | 83.6% | 54.3% | 49.9% | 49.6% |
| Triester content [%] | max. 3.00 | 1.6% | 5.4% | 27.8% | 33.1% | 33.4% |

-continued

| Storage stability at 30° C. | Start | 1 month | 3 months | 6 months | 8 months |
|---|---|---|---|---|---|
| Benzoic acid [%] | 0.51% | n.d. | n.d. | n.d. | n.d. |
| Glycidyl methacrylate [%] | 0.62% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 88.1% | 50.2% | 48.0% | 48.3% | 48.1% |
| Triester content [%] | max. 3.00 | 1.6% | 31.7% | 33.3% | 33.5% | 33.3% |
| Benzoic acid [%] | | 0.51% | n.d. | n.d. | n.d. | n.d. |
| Glycidyl methacrylate [%] | | 0.62% | n.d. | n.d. | n.d. | n.d. |

Conclusion: The product prepared with a molar stoichiometry of 1:1 at the end of the reactant addition proved to be NOT storage-stable!

Inventive Example 15

Molar Stoichiometry (Glycidyl Methacrylate:Carboxylic Acid) 1:1.02

Method is distinguished in that the procedure is carried out analogously to Example 1 but 262.9 g of benzoic acid is used as carboxylic acid.

| Storage stability at 30° C. | | Start | 1 month | 3 months | 6 months | 8 months |
|---|---|---|---|---|---|---|
| Diester content [%] | min. 85.00 | 88.3% | 89.0% | 88.8% | 88.9% | 88.3% |
| Triester content [%] | max. 3.00 | 1.2% | 1.3% | 1.2% | 1.4% | 1.6% |
| Benzoic acid [%] | | 0.55% | n.d. | n.d. | n.d. | n.d. |
| Glycidyl methacrylate [%] | | 0.56% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 88.3% | 88.5% | 88.3% | 87.8% | 86.3% |
| Triester content [%] | max. 3.00 | 1.2% | 1.5% | 1.7% | 2.2% | 2.5% |
| Benzoic acid [%] | | 0.55% | n.d. | n.d. | n.d. | n.d. |
| Glycidyl methacrylate [%] | | 0.56% | n.d. | n.d. | n.d. | n.d. |

Conclusion: The product prepared with a molar stoichiometry of 1:1.02 at the end of the reactant addition had a storage stability of more than 8 months.

Preparation Example 16

Method is distinguished in that the procedure is carried out analogously to Example 1 but 287.1 g of salicylic acid as carboxylic acid and a solvent are used.
Molar Stoichiometry (Glycidyl Methacrylate:Carboxylic Acid) 1:0.985

| Storage stability at 30° C. | | | | | | |
|---|---|---|---|---|---|---|
| | | Start | 1 month | 3 months | 6 months | 8 months |
| Diester content [%] | min. 85.00 | 88.7% | 84.2% | 54.6% | 50.2% | 49.9% |
| Triester content [%] | max. 3.00 | 1.4% | 4.7% | 24.1% | 28.6% | 28.9% |
| Salicylic acid [%] | | 0.52% | n.d. | n.d. | n.d. | n.d. |

-continued

| Storage stability at 30° C. | | | | | |
|---|---|---|---|---|---|
| | Start | 1 month | 3 months | 6 months | 8 months |
| Glycidyl methacrylate [%] | 0.64% | n.d. | n.d. | n.d. | n.d. |

| Storage stability at 50° C. | | | | | | |
|---|---|---|---|---|---|---|
| | | Start | 1 month | 3 months | 6 months | 8 months |
| Diester content [%] | min. 85.00 | 88.7% | 50.6% | 48.3% | 48.6% | 48.5% |
| Triester content [%] | max. 3.00 | 1.4% | 27.4% | 28.8% | 29.0% | 28.8% |
| Salicylic acid [%] | | 0.52% | n.d. | n.d. | n.d. | n.d. |
| Glycidyl methacrylate [%] | | 0.64% | n.d. | n.d. | n.d. | n.d. |

Conclusion: The product prepared with a molar stoichiometry of 1:0.985 at the end of the reactant addition proved to be NOT storage-stable!

Preparation Example 17

Molar Stoichiometry (Glycidyl Methacrylate:Carboxylic Acid) 1:1

Method is distinguished in that the procedure is carried out analogously to Example 1 but 291.5 g of salicylic acid as carboxylic acid and a solvent are used.

| Storage stability at 30° C. | | | | | | |
|---|---|---|---|---|---|---|
| | | Start | 1 month | 3 months | 6 months | 8 months |
| Diester content [%] | min. 85.00 | 89.6% | 85.0% | 55.2% | 50.7% | 50.4% |
| Triester content [%] | max. 3.00 | 1.8% | 6.2% | 32.0% | 37.9% | 38.4% |
| Salicylic acid [%] | | 0.55% | n.d. | n.d. | n.d. | n.d. |
| Glycidyl methacrylate [%] | | 0.59% | n.d. | n.d. | n.d. | n.d. |

| Storage stability at 50° C. | | | | | | |
|---|---|---|---|---|---|---|
| | | Start | 1 month | 3 months | 6 months | 8 months |
| Diester content [%] | min. 85.00 | 89.6% | 51.1% | 48.8% | 49.1% | 48.9% |
| Triester content [%] | max. 3.00 | 1.8% | 36.4% | 38.2% | 38.5% | 38.2% |
| Salicylic acid [%] | | 0.55% | n.d. | n.d. | n.d. | n.d. |
| Glycidyl methacrylate [%] | | 0.59% | n.d. | n.d. | n.d. | n.d. |

Conclusion: The product prepared with a molar stoichiometry of 1:1 at the end of the reactant addition proved to be NOT storage-stable!

Inventive Example 18

Molar Stoichiometry (Glycidyl Methacrylate:Carboxylic Acid) 1:1.02

Method is distinguished in that the procedure is carried out analogously to Example 1 but 297.3 g of salicylic acid as carboxylic acid and a solvent are used.

Storage stability at 30° C.

|  |  | Start | 1 month | 3 months | 6 months | 8 months |
|---|---|---|---|---|---|---|
| Diester content [%] | min. 85.00 | 89.7% | 90.4.% | 90.2% | 90.4% | 89.7% |
| Triester content [%] | max. 3.00 | 1.4% | 1.5% | 1.4% | 1.6% | 1.8% |
| Salicylic acid [%] |  | 0.59% | n.d. | n.d. | n.d. | n.d. |
| Glycidyl methacrylate [%] |  | 0.53% | n.d. | n.d. | n.d. | n.d. |

Storage stability at 50° C.

|  |  | Start | 1 month | 3 months | 6 months | 8 months |
|---|---|---|---|---|---|---|
| Diester content [%] | min. 85.00 | 89.7% | 89.9% | 89.7% | 89.2% | 87.7% |
| Triester content [%] | max. 3.00 | 1.4% | 1.7% | 2.0% | 2.5% | 2.9% |
| Salicylic acid [%] |  | 0.59% | n.d. | n.d. | n.d. | n.d. |
| Glycidyl methacrylate [%] |  | 0.53% | n.d. | n.d. | n.d. | n.d. |

Conclusion: The product prepared with a molar stoichiometry of 1:1.02 at the end of the reactant addition had a storage stability of more than 8 months.

Preparation Example 19

Method is distinguished in that the procedure is carried out analogously to Example 1 but 255.9 g of nicotinic acid as carboxylic acid and a solvent are used.
Molar Stoichiometry (Glycidyl Methacrylate:Carboxylic Acid) 1:0.985

Storage stability at 30° C.

|  |  | Start | 1 month | 3 months | 6 months | 8 months |
|---|---|---|---|---|---|---|
| Diester content [%] | min. 85.00 | 87.6% | 83.1% | 53.9% | 49.6% | 49.3% |
| Triester content [%] | max. 3.00 | 1.6% | 5.4% | 27.9% | 33.1% | 33.5% |
| Nicotinic acid [%] |  | 0.49% | n.d. | n.d. | n.d. | n.d. |
| Glycidyl methacrylate [%] |  | 0.67% | n.d. | n.d. | n.d. | n.d. |

Storage stability at 50° C.

|  |  | Start | 1 month | 3 months | 6 months | 8 months |
|---|---|---|---|---|---|---|
| Diester content [%] | min. 85.00 | 87.6% | 49.9% | 47.7% | 48.0% | 47.8% |
| Triester content [%] | max. 3.00 | 1.6% | 31.7% | 33.4% | 33.5% | 33.3% |
| Nicotinic acid [%] |  | 0.49% | n.d. | n.d. | n.d. | n.d. |
| Glycidyl methacrylate [%] |  | 0.67% | n.d. | n.d. | n.d. | n.d. |

Conclusion: The product prepared with a molar stoichiometry of 1:0.985 at the end of the reactant addition proved to be NOT storage-stable!

Preparation Example 20

Molar Stoichiometry (Glycidyl Methacrylate:Carboxylic Acid) 1:1

Method is distinguished in that the procedure is carried out analogously to Example 1 but 259.8 g of nicotinic acid as carboxylic acid and a solvent are used.

Storage stability at 30° C.

|  |  | Start | 1 month | 3 months | 6 months | 8 months |
|---|---|---|---|---|---|---|
| Diester content [%] | min. 85.00 | 87.0% | 82.5% | 53.6% | 49.2% | 48.9% |
| Triester content [%] | max. 3.00 | 1.8% | 5.9% | 30.7% | 36.5% | 36.9% |
| Nicotinic acid [%] |  | 0.51% | n.d. | n.d. | n.d. | n.d. |
| Glycidyl methacrylate [%] |  | 0.62% | n.d. | n.d. | n.d. | n.d. |

Storage stability at 50° C.

|  |  | Start | 1 month | 3 months | 6 months | 8 months |
|---|---|---|---|---|---|---|
| Diester content [%] | min. 85.00 | 87.0% | 49.6% | 47.3% | 47.7% | 47.5% |
| Triester content [%] | max. 3.00 | 1.8% | 35.0% | 36.8% | 37.0% | 36.7% |
| Nicotinic acid [%] |  | 0.51% | n.d. | n.d. | n.d. | n.d. |
| Glycidyl methacrylate [%] |  | 0.62% | n.d. | n.d. | n.d. | n.d. |

Conclusion: The product prepared with a molar stoichiometry of 1:1 at the end of the reactant addition proved to be NOT storage-stable!

Inventive Example 21

Molar Stoichiometry (Glycidyl Methacrylate:Carboxylic Acid) 1:1.02

Method is distinguished in that the procedure is carried out analogously to Example 1 but 265 g of nicotinic acid as carboxylic acid and a solvent are used.

Storage stability at 30° C.

|  |  | Start | 1 month | 3 months | 6 months | 8 months |
|---|---|---|---|---|---|---|
| Diester content [%] | min. 85.00 | 89.2% | 89.9% | 89.7% | 89.8% | 89.2% |
| Triester content [%] | max. 3.00 | 2.0% | 2.0% | 2.0% | 2.2% | 2.5% |
| Nicotinic acid [%] |  | 0.55% | n.d. | n.d. | n.d. | n.d. |
| Glycidyl methacrylate [%] |  | 0.56% | n.d. | n.d. | n.d. | n.d. |

Storage stability at 50° C.

|  |  | Start | 1 month | 3 months | 6 months | 8 months |
|---|---|---|---|---|---|---|
| Diester content [%] | min. 85.00 | 89.2% | 89.3% | 89.2% | 88.6% | 87.1% |
| Triester content [%] | max. 3.00 | 2.0% | 2.3% | 2.7% | 3.0% | 3.7% |
| Nicotinic acid [%] |  | 0.55% | n.d. | n.d. | n.d. | n.d. |
| Glycidyl methacrylate [%] |  | 0.56% | n.d. | n.d. | n.d. | n.d. |

Conclusion: The product prepared with a molar stoichiometry of 1:1.02 at the end of the reactant addition had a storage stability of more than 6 months.

Preparation Example 22

Method is distinguished in that the procedure is carried out analogously to Example 1 but 239.3 g of proline as carboxylic acid and a solvent are used.

Molar Stoichiometry (Glycidyl Methacrylate:Carboxylic Acid) 1:0.985

| Storage stability at 30° C. | | | | | | |
|---|---|---|---|---|---|---|
|  |  | Start | 1 month | 3 months | 6 months | 8 months |
| Diester content [%] | min. 85.00 | 88.6% | 84.1% | 54.6% | 50.2% | 49.9% |
| Triester content [%] | max. 3.00 | 1.9% | 6.3% | 32.6% | 38.7% | 39.1% |
| Proline [%] |  | 0.47% | n.d. | n.d. | n.d. | n.d. |
| Glycidyl methacrylate [%] |  | 0.70% | n.d. | n.d. | n.d. | n.d. |

| Storage stability at 50° C. | | | | | | |
|---|---|---|---|---|---|---|
|  |  | Start | 1 month | 3 months | 6 months | 8 months |
| Diester content [%] | min. 85.00 | 88.6% | 50.5% | 48.2% | 48.6% | 48.4% |
| Triester content [%] | max. 3.00 | 1.9% | 37.1% | 39.0% | 39.2% | 39.0% |
| Proline [%] |  | 0.47% | n.d. | n.d. | n.d. | n.d. |
| Glycidyl methacrylate [%] |  | 0.70% | n.d. | n.d. | n.d. | n.d. |

Conclusion: The product prepared with a molar stoichiometry of 1:0.985 at the end of the reactant addition proved to be NOT storage-stable!

Preparation Example 23

Molar Stoichiometry (Glycidyl Methacrylate:Carboxylic Acid) 1:1

Method is distinguished in that the procedure is carried out analogously to Example 1 but 243 g of proline as carboxylic acid and a solvent are used.

| Storage stability at 30° C. | | | | | | |
|---|---|---|---|---|---|---|
|  |  | Start | 1 month | 3 months | 6 months | 8 months |
| Diester content [%] | min. 85.00 | 89.0% | 84.4% | 54.8% | 50.4% | 50.1% |
| Triester content [%] | max. 3.00 | 1.8% | 5.9% | 30.3% | 36.0% | 36.3% |
| Proline [%] |  | 0.50% | n.d. | n.d. | n.d. | n.d. |
| Glycidyl methacrylate [%] |  | 0.64% | n.d. | n.d. | n.d. | n.d. |

| Storage stability at 50° C. |  | Start | 1 month | 3 months | 6 months | 8 months |
|---|---|---|---|---|---|---|
| Diester content [%] | min. 85.00 | 89.0% | 50.7% | 48.4% | 48.8% | 48.6% |
| Triester content [%] | max. 3.00 | 1.8% | 34.5% | 36.2% | 36.4% | 36.2% |
| Proline [%] |  | 0.50% | n.d. | n.d. | n.d. | n.d. |
| Glycidyl methacrylate [%] |  | 0.64% | n.d. | n.d. | n.d. | n.d. |

Conclusion: The product prepared with a molar stoichiometry of 1:1 at the end of the reactant addition proved to be NOT storage-stable!

Inventive Example 24

Molar Stoichiometry (Glycidyl Methacrylate:Carboxylic Acid) 1:1.02

Method is distinguished in that the procedure is carried out analogously to Example 1 but 247.8 g of proline as carboxylic acid and a solvent are used.

| Storage stability at 30° C. | | Start | 1 month | 3 months | 6 months | 8 months |
|---|---|---|---|---|---|---|
| Diester content [%] | min. 85.00 | 85.6% | 86.3% | 86.1% | 86.2% | 85.6% |
| Triester content [%] | max. 3.00 | 1.1% | 1.1% | 1.1% | 1.2% | 1.4% |
| Proline [%] | | 0.53% | n.d. | n.d. | n.d. | n.d. |
| Glycidyl methacrylate [%] | | 0.58% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 85.6% | 85.7% | 85.6% | 85.1% | 83.6% |
| Triester content [%] | max. 3.00 | 1.1% | 1.3% | 1.5% | 1.9% | 2.2% |
| Proline [%] | | 0.53% | n.d. | n.d. | n.d. | n.d. |
| Glycidyl methacrylate [%] | | 0.58% | n.d. | n.d. | n.d. | n.d. |

Conclusion: The product prepared with a molar stoichiometry of 1:1.02 at the end of the reactant addition had a storage stability of more than 6 months.

Preparation Example 25

Method is distinguished in that the procedure is carried out analogously to Example 1 but 149.8 g of acrylic acid is used as carboxylic acid.
Molar Stoichiometry (Glycidyl Methacrylate:Carboxylic Acid) 1:0.985

| Storage stability at 30° C. | | Start | 1 month | 3 months | 6 months | 8 months |
|---|---|---|---|---|---|---|
| Diester content [%] | min. 85.00 | 89.0% | 84.4% | 54.8% | 50.4% | 50.1% |
| Triester content [%] | max. 3.00 | 1.4% | 4.6% | 23.8% | 28.3% | 28.6% |
| Acrylic acid [%] | | 0.36% | n.d. | n.d. | n.d. | n.d. |
| Glycidyl methacrylate [%] | | 0.83% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 89.0% | 50.7% | 48.4% | 48.8% | 48.6% |
| Triester content [%] | max. 3.00 | 1.4% | 27.1% | 28.5% | 28.7% | 28.5% |
| Acrylic acid [%] | | 0.36% | n.d. | n.d. | n.d. | n.d. |
| Glycidyl methacrylate [%] | | 0.83% | n.d. | n.d. | n.d. | n.d. |

Conclusion: The product prepared with a molar stoichiometry of 1:0.985 at the end of the reactant addition proved to be NOT storage-stable!

Preparation Example 26

Molar Stoichiometry (Glycidyl Methacrylate:Carboxylic Acid) 1:1
Method is distinguished in that the procedure is carried out analogously to Example 1 but 152.1 g of acrylic acid is used as carboxylic acid.

| Storage stability at 30° C. | | Start | 1 month | 3 months | 6 months | 8 months |
|---|---|---|---|---|---|---|
| Diester content [%] | min. 85.00 | 88.2% | 83.7% | 54.3% | 49.9% | 49.6% |
| Triester content [%] | max. 3.00 | 1.8% | 6.0% | 30.9% | 36.7% | 37.1% |
| Acrylic acid [%] | | 0.37% | n.d. | n.d. | n.d. | n.d. |
| Glycidyl methacrylate [%] | | 0.77% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 88.2% | 50.3% | 48.0% | 48.3% | 48.2% |
| Triester content [%] | max. 3.00 | 1.8% | 35.2% | 37.0% | 37.2% | 36.9% |
| Acrylic acid [%] | | 0.37% | n.d. | n.d. | n.d. | n.d. |
| Glycidyl methacrylate [%] | | 0.77% | n.d. | n.d. | n.d. | n.d. |

Conclusion: The product prepared with a molar stoichiometry of 1:1 at the end of the reactant addition proved to be NOT storage-stable!

Inventive Example 27

Molar Stoichiometry (Glycidyl Methacrylate:Carboxylic Acid) 1:1.02

Method is distinguished in that the procedure is carried out analogously to Example 1 but 155.1 g of acrylic acid is used as carboxylic acid.

| Storage stability at 30° C. | | Start | 1 month | 3 months | 6 months | 8 months |
|---|---|---|---|---|---|---|
| Diester content [%] | min. 85.00 | 88.3% | 89.0% | 88.8% | 88.9% | 88.3% |
| Triester content [%] | max. 3.00 | 1.8% | 1.9% | 1.8% | 2.0% | 2.3% |
| Acrylic acid [%] | | 0.40% | n.d. | n.d. | n.d. | n.d. |
| Glycidyl methacrylate [%] | | 0.69% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 88.3% | 88.4% | 88.3% | 87.7% | 86.2% |
| Triester content [%] | max. 3.00 | 1.8% | 2.2% | 2.4% | 2.7% | 3.0% |
| Acrylic acid [%] | | 0.40% | n.d. | n.d. | n.d. | n.d. |
| Glycidyl methacrylate [%] | | 0.69% | n.d. | n.d. | n.d. | n.d. |

Conclusion: The product prepared with a molar stoichiometry of 1:1.02 at the end of the reactant addition had a storage stability of more than 8 months.

Preparation Example 28

Method is distinguished in that the procedure is carried out analogously to Example 1 but 587.2 g of oleic acid is used as carboxylic acid.
Molar Stoichiometry (Glycidyl Methacrylate:Carboxylic Acid) 1:0.985

| Storage stability at 30° C. | | Start | 1 month | 3 months | 6 months | 8 months |
|---|---|---|---|---|---|---|
| Diester content [%] | min. 85.00 | 87.6% | 83.1% | 53.9% | 49.6% | 49.3% |
| Triester content [%] | max. 3.00 | 1.2% | 4.1% | 21.4% | 25.4% | 25.6% |
| Oleic acid [%] | | 0.71% | n.d. | n.d. | n.d. | n.d. |
| Glycidyl methacrylate [%] | | 0.42% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 87.6% | 49.9% | 47.7% | 48.0% | 47.8% |
| Triester content [%] | max. 3.00 | 1.2% | 24.3% | 25.6% | 25.7% | 25.5% |
| Oleic acid [%] | | 0.71% | n.d. | n.d. | n.d. | n.d. |
| Glycidyl methacrylate [%] | | 0.42% | n.d. | n.d. | n.d. | n.d. |

Conclusion: The product prepared with a molar stoichiometry of 1:0.985 at the end of the reactant addition proved to be NOT storage-stable!

Preparation Example 29

Molar Stoichiometry (Glycidyl Methacrylate:Carboxylic Acid) 1:1

Method is distinguished in that the procedure is carried out analogously to Example 1 but 596.1 g of oleic acid is used as carboxylic acid.

| Storage stability at 30° C. | | Start | 1 month | 3 months | 6 months | 8 months |
|---|---|---|---|---|---|---|
| Diester content [%] | min. 85.00 | 89.1% | 84.6% | 54.9% | 50.4% | 50.2% |
| Triester content [%] | max. 3.00 | 1.1% | 3.8% | 19.7% | 23.4% | 23.7% |
| Oleic acid [%] | | 0.74% | n.d. | n.d. | n.d. | n.d. |
| Glycidyl methacrylate [%] | | 0.39% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 89.1% | 50.8% | 48.5% | 48.8% | 48.7% |
| Triester content [%] | max. 3.00 | 1.1% | 22.5% | 23.6% | 23.8% | 23.6% |
| Oleic acid [%] | | 0.74% | n.d. | n.d. | n.d. | n.d. |
| Glycidyl methacrylate [%] | | 0.39% | n.d. | n.d. | n.d. | n.d. |

Conclusion: The product prepared with a molar stoichiometry of 1:1 at the end of the reactant addition proved to be NOT storage-stable!

Inventive Example 30

Molar Stoichiometry (Glycidyl Methacrylate:Carboxylic Acid) 1:1.02

Method is distinguished in that the procedure is carried out analogously to Example 1 but 608 g of oleic acid is used as carboxylic acid.

| Storage stability at 30° C. | | Start | 1 month | 3 months | 6 months | 8 months |
|---|---|---|---|---|---|---|
| Diester content [%] | min. 85.00 | 87.7% | 88.4% | 88.2% | 88.3% | 87.8% |
| Triester content [%] | max. 3.00 | 1.4% | 1.4% | 1.4% | 1.5% | 1.8% |
| Oleic acid [%] | | 0.79% | n.d. | n.d. | n.d. | n.d. |
| Glycidyl methacrylate [%] | | 0.35% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 87.7% | 87.8% | 87.7% | 87.1% | 85.7% |
| Triester content [%] | max. 3.00 | 1.4% | 1.7% | 1.9% | 2.4% | 2.8% |
| Oleic acid [%] | | 0.79% | n.d. | n.d. | n.d. | n.d. |
| Glycidyl methacrylate [%] | | 0.35% | n.d. | n.d. | n.d. | n.d. |

Conclusion: The product prepared with a molar stoichiometry of 1:1.02 at the end of the reactant addition had a storage stability of more than 8 months.

Preparation Example 31

Method is distinguished in that the procedure is carried out analogously to Example 1 but 187.3 g of lactic acid is used as carboxylic acid.

Molar Stoichiometry (Glycidyl Methacrylate:Carboxylic Acid) 1:0.985

| Storage stability at 30° C. | | | | | | |
|---|---|---|---|---|---|---|
| | | Start | 1 month | 3 months | 6 months | 8 months |
| Diester content [%] | min. 85.00 | 89.0% | 84.4% | 54.8% | 50.4% | 50.1% |
| Triester content [%] | max. 3.00 | 1.0% | 3.5% | 18.0% | 21.4% | 21.7% |
| Lactic acid [%] | | 0.41% | n.d. | n.d. | n.d. | n.d. |
| Glycidyl methacrylate [%] | | 0.77% | n.d. | n.d. | n.d. | n.d. |

| Storage stability at 50° C. | | | | | | |
|---|---|---|---|---|---|---|
| | | Start | 1 month | 3 months | 6 months | 8 months |
| Diester content [%] | min. 85.00 | 89.0% | 50.7% | 48.4% | 48.8% | 48.6% |
| Triester content [%] | max. 3.00 | 1.0% | 20.5% | 21.6% | 21.7% | 21.6% |
| Lactic acid [%] | | 0.41% | n.d. | n.d. | n.d. | n.d. |
| Glycidyl methacrylate [%] | | 0.77% | n.d. | n.d. | n.d. | n.d. |

Conclusion: The product prepared with a molar stoichiometry of 1:0.985 at the end of the reactant addition proved to be NOT storage-stable!

Preparation Example 32

Molar Stoichiometry (Glycidyl Methacrylate:Carboxylic Acid) 1:1

Method is distinguished in that the procedure is carried out analogously to Example 1 but 190.1 g of lactic acid is used as carboxylic acid.

| Storage stability at 30° C. | | | | | | |
|---|---|---|---|---|---|---|
| | | Start | 1 month | 3 months | 6 months | 8 months |
| Diester content [%] | min. 85.00 | 89.3% | 84.8% | 55.0% | 50.6% | 50.3% |
| Triester content [%] | max. 3.00 | 1.6% | 5.2% | 27.0% | 32.1% | 32.4% |
| Lactic acid [%] | | 0.43% | n.d. | n.d. | n.d. | n.d. |
| Glycidyl methacrylate [%] | | 0.71% | n.d. | n.d. | n.d. | n.d. |

| Storage stability at 50° C. | | | | | | |
|---|---|---|---|---|---|---|
| | | Start | 1 month | 3 months | 6 months | 8 months |
| Diester content [%] | min. 85.00 | 89.3% | 50.9% | 48.6% | 49.0% | 48.8% |
| Triester content [%] | max. 3.00 | 1.6% | 30.8% | 32.3% | 32.5% | 32.3% |
| Lactic acid [%] | | 0.43% | n.d. | n.d. | n.d. | n.d. |
| Glycidyl methacrylate [%] | | 0.71% | n.d. | n.d. | n.d. | n.d. |

Conclusion: The product prepared with a molar stoichiometry of 1:1 at the end of the reactant addition proved to be NOT storage-stable!

Inventive Example 33

Molar Stoichiometry (Glycidyl Methacrylate:Carboxylic Acid) 1:1.02

Method is distinguished in that the procedure is carried out analogously to Example 1 but 193.9 g of lactic acid is used as carboxylic acid.

| Storage stability at 30° C. | | | | | | |
|---|---|---|---|---|---|---|
| | | Start | 1 month | 3 months | 6 months | 8 months |
| Diester content [%] | min. 85.00 | 85.6% | 86.3% | 86.1% | 86.2% | 85.6% |
| Triester content [%] | max. 3.00 | 1.4% | 1.4% | 1.4% | 1.5% | 1.7% |
| Lactic acid [%] | | 0.46% | n.d. | n.d. | n.d. | n.d. |
| Glycidyl methacrylate [%] | | 0.64% | n.d. | n.d. | n.d. | n.d. |

| Storage stability at 50° C. | | | | | | |
|---|---|---|---|---|---|---|
| | | Start | 1 month | 3 months | 6 months | 8 months |
| Diester content [%] | min. 85.00 | 85.6% | 85.7% | 85.6% | 85.1% | 83.6% |
| Triester content [%] | max. 3.00 | 1.4% | 1.6% | 1.9% | 2.4% | 2.8% |
| Lactic acid [%] | | 0.46% | n.d. | n.d. | n.d. | n.d. |
| Glycidyl methacrylate [%] | | 0.64% | n.d. | n.d. | n.d. | n.d. |

Conclusion: The product prepared with a molar stoichiometry of 1:1.02 at the end of the reactant addition had a storage stability of more than 6 months.

Preparation Example 34

Method is distinguished in that the procedure is carried out analogously to Example 1 but 216.4 g of hydroxyisobutyric acid is used as carboxylic acid.
Molar Stoichiometry (Glycidyl Methacrylate:Carboxylic Acid) 1:0.985

| Storage stability at 30° C. | | | | | | |
|---|---|---|---|---|---|---|
| | | Start | 1 month | 3 months | 6 months | 8 months |
| Diester content [%] | min. 85.00 | 87.0% | 82.5% | 53.6% | 49.2% | 48.9% |
| Triester content [%] | max. 3.00 | 1.7% | 5.8% | 30.2% | 35.9% | 36.2% |
| Hydroxyisobutyric acid [%] | | 0.45% | n.d. | n.d. | n.d. | n.d. |
| Glycidyl methacrylate [%] | | 0.73% | n.d. | n.d. | n.d. | n.d. |

| Storage stability at 50° C. | | | | | | |
|---|---|---|---|---|---|---|
| | | Start | 1 month | 3 months | 6 months | 8 months |
| Diester content [%] | min. 85.00 | 87.0% | 49.6% | 47.4% | 47.7% | 47.5% |
| Triester content [%] | max. 3.00 | 1.7% | 34.4% | 36.1% | 36.3% | 36.1% |
| Hydroxyisobutyric acid [%] | | 0.45% | n.d. | n.d. | n.d. | n.d. |
| Glycidyl methacrylate [%] | | 0.73% | n.d. | n.d. | n.d. | n.d. |

Conclusion: The product prepared with a molar stoichiometry of 1:0.985 at the end of the reactant addition proved to be NOT storage-stable!

Preparation Example 35

Molar Stoichiometry (Glycidyl Methacrylate:Carboxylic Acid) 1:1
Method is distinguished in that the procedure is carried out analogously to Example 1 but 219.7 g of hydroxyisobutyric acid is used as carboxylic acid.

| Storage stability at 30° C. | | | | | | |
|---|---|---|---|---|---|---|
| | | Start | 1 month | 3 months | 6 months | 8 months |
| Diester content [%] | min. 85.00 | 87.4% | 83.0% | 53.8% | 49.5% | 49.2% |
| Triester content [%] | max. 3.00 | 1.3% | 4.4% | 22.6% | 26.8% | 27.1% |
| Hydroxyisobutyric acid [%] | | 0.47% | n.d. | n.d. | n.d. | n.d. |
| Glycidyl methacrylate [%] | | 0.67% | n.d. | n.d. | n.d. | n.d. |

| Storage stability at 50° C. | | | | | | |
|---|---|---|---|---|---|---|
| | | Start | 1 month | 3 months | 6 months | 8 months |
| Diester content [%] | min. 85.00 | 87.4% | 49.8% | 47.6% | 47.9% | 47.8% |
| Triester content [%] | max. 3.00 | 1.3% | 25.7% | 27.0% | 27.2% | 27.0% |
| Hydroxyisobutyric acid [%] | | 0.47% | n.d. | n.d. | n.d. | n.d. |
| Glycidyl methacrylate [%] | | 0.67% | n.d. | n.d. | n.d. | n.d. |

Conclusion: The product prepared with a molar stoichiometry of 1:1 at the end of the reactant addition proved to be NOT storage-stable!

Inventive Example 36

Molar Stoichiometry (Glycidyl Methacrylate:Carboxylic Acid) 1:1.02

Method is distinguished in that the procedure is carried out analogously to Example 1 but 224.1 g of hydroxyisobutyric acid is used as carboxylic acid.

| Storage stability at 30° C. | | | | | | |
|---|---|---|---|---|---|---|
| | | Start | 1 month | 3 months | 6 months | 8 months |
| Diester content [%] | min. 85.00 | 88.1% | 88.8% | 88.6% | 88.7% | 88.1% |
| Triester content [%] | max. 3.00 | 1.7% | 1.7% | 1.7% | 1.9% | 2.1% |
| Hydroxyisobutyric acid [%] | | 0.50% | n.d. | n.d. | n.d. | n.d. |
| Glycidyl methacrylate [%] | | 0.60% | n.d. | n.d. | n.d. | n.d. |

| Storage stability at 50° C. | | | | | | |
|---|---|---|---|---|---|---|
| | | Start | 1 month | 3 months | 6 months | 8 months |
| Diester content [%] | min. 85.00 | 88.1% | 88.2% | 88.1% | 87.5% | 86.0% |
| Triester content [%] | max. 3.00 | 1.7% | 2.0% | 2.3% | 3.0% | 3.4% |
| Hydroxyisobutyric acid [%] | | 0.50% | n.d. | n.d. | n.d. | n.d. |
| Glycidyl methacrylate [%] | | 0.60% | n.d. | n.d. | n.d. | n.d. |

Conclusion: The product prepared with a molar stoichiometry of 1:1.02 at the end of the reactant addition had a storage stability of more than 6 months.

Preparation Example 37

Method is distinguished in that the procedure is carried out analogously to Example 1 but 339.7 g of trichloroacetic acid is used as carboxylic acid.

Molar Stoichiometry (Glycidyl Methacrylate:Carboxylic Acid) 1:0.985

| Storage stability at 30° C. | | Start | 1 month | 3 months | 6 months | 8 months |
|---|---|---|---|---|---|---|
| Diester content [%] | min. 85.00 | 87.5% | 83.0% | 53.9% | 49.5% | 49.2% |
| Triester content [%] | max. 3.00 | 1.4% | 4.8% | 25.0% | 29.7% | 30.0% |
| Trichloroacetic acid [%] | | 0.57% | n.d. | n.d. | n.d. | n.d. |
| Glycidyl methacrylate [%] | | 0.59% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 87.5% | 49.8% | 47.6% | 47.9% | 47.8% |
| Triester content [%] | max. 3.00 | 1.4% | 28.4% | 29.9% | 30.1% | 29.9% |
| Trichloroacetic acid [%] | | 0.57% | n.d. | n.d. | n.d. | n.d. |
| Glycidyl methacrylate [%] | | 0.59% | n.d. | n.d. | n.d. | n.d. |

Conclusion: The product prepared with a molar stoichiometry of 1:0.985 at the end of the reactant addition proved to be NOT storage-stable!

Preparation Example 38

Molar Stoichiometry (Glycidyl Methacrylate:Carboxylic Acid) 1:1

Method is distinguished in that the procedure is carried out analogously to Example 1 but 344.8 g of trichloroacetic acid is used as carboxylic acid.

| Storage stability at 30° C. | | Start | 1 month | 3 months | 6 months | 8 months |
|---|---|---|---|---|---|---|
| Diester content [%] | min. 85.00 | 88.0% | 83.5% | 54.2% | 49.8% | 49.5% |
| Triester content [%] | max. 3.00 | 1.7% | 5.8% | 29.9% | 35.5% | 35.9% |
| Trichloroacetic acid [%] | | 0.59% | n.d. | n.d. | n.d. | n.d. |
| Glycidyl methacrylate [%] | | 0.54% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 88.0% | 50.1% | 47.9% | 48.2% | 48.0% |
| Triester content [%] | max. 3.00 | 1.7% | 34.1% | 35.8% | 36.0% | 35.8% |
| Trichloroacetic acid [%] | | 0.59% | n.d. | n.d. | n.d. | n.d. |
| Glycidyl methacrylate [%] | | 0.54% | n.d. | n.d. | n.d. | n.d. |

Conclusion: The product prepared with a molar stoichiometry of 1:1 at the end of the reactant addition proved to be NOT storage-stable!

Inventive Example 39

Molar Stoichiometry (Glycidyl Methacrylate:Carboxylic Acid) 1:1.02

Method is distinguished in that the procedure is carried out analogously to Example 1 but 351.7 g of trichloroacetic acid is used as carboxylic acid.

| Storage stability at 30° C. | | Start | 1 month | 3 months | 6 months | 8 months |
|---|---|---|---|---|---|---|
| Diester content [%] | min. 85.00 | 85.6% | 86.3% | 86.1% | 86.2% | 85.6% |
| Triester content [%] | max. 3.00 | 1.6% | 1.6% | 1.6% | 1.8% | 2.0% |
| Trichloroacetic acid [%] | | 0.64% | n.d. | n.d. | n.d. | n.d. |
| Glycidyl methacrylate [%] | | 0.48% | n.d. | n.d. | n.d. | n.d. |

| Storage stability at 50° C. | | Start | 1 month | 3 months | 6 months | 8 months |
|---|---|---|---|---|---|---|
| Diester content [%] | min. 85.00 | 85.6% | 85.7% | 85.6% | 85.1% | 83.6% |
| Triester content [%] | max. 3.00 | 1.6% | 1.9% | 2.2% | 2.8% | 3.3% |
| Trichloroacetic acid [%] | | 0.64% | n.d. | n.d. | n.d. | n.d. |
| Glycidyl methacrylate [%] | | 0.48% | n.d. | n.d. | n.d. | n.d. |

Conclusion: The product prepared with a molar stoichiometry of 1:1.02 at the end of the reactant addition had a storage stability of more than 3 months.

Inventive Example 40

Post-Stabilization with Carboxylic Acid Endogenous to the System Prior to Storage Method according to Example 1, distinguished in that 179 g of methacrylic acid is used as carboxylic acid and at the end of the reactant addition the molar stoichiometry (glycidyl methacrylate:carboxylic acid) is 1:0.985.

Prior to storage, the crude product obtained is doped with 1.5 g of methacrylic acid.

Molar Stoichiometry Prior to Storage: Glycidyl Methacrylate<Carboxylic Acid

| Storage stability at 30° C. | | Product | Start | 1 month | 3 months | 6 months | 8 months |
|---|---|---|---|---|---|---|---|
| Diester content [%] | min. 85.00 | 86.10% | 85.84% | 86.47% | 86.28% | 86.39% | 85.77% |
| Triester content [%] | max. 3.00 | 1.60% | 1.59% | 1.58% | 1.53% | 1.69% | 1.94% |
| Methacrylic acid [%] | | 0.40% | 0.71% | n.d. | n.d. | n.d. | n.d. |
| Glycidyl methacrylate [%] | | 0.78% | 0.78% | n.d. | n.d. | n.d. | n.d. |

| Storage stability at 50° C. | | Product | Start | 1 month | 3 months | 6 months | 8 months |
|---|---|---|---|---|---|---|---|
| Diester content [%] | min. 85.00 | 86.10% | 85.84% | 85.94% | 85.81% | 85.26% | 83.81% |
| Triester content [%] | max. 3.00 | 1.60% | 1.59% | 1.82% | 2.10% | 2.68% | 3.12% |

| Storage stability at 50° C. | Product | Start | 1 month | 3 months | 6 months | 8 months |
|---|---|---|---|---|---|---|
| Methacrylic acid [%] | 0.40% | 0.71% | n.d. | n.d. | n.d. | n.d. |
| Glycidyl methacrylate [%] | 0.78% | 0.78% | n.d. | n.d. | n.d. | n.d. |

Conclusion: The crude product prepared with a molar stoichiometry of 1:0.985 at the end of the reactant addition, but post-stabilized, had a storage stability of 6 months, whereas the non-stabilized reference sample of Example 1 was not storage-stable.

Inventive Example 41

Post-Stabilization with Carboxylic Acid Endogenous to the System Prior to Storage Method according to Example 2, distinguished in that 181.7 g of methacrylic acid is used as carboxylic acid and at the end of the reactant addition the molar stoichiometry (glycidyl methacrylate:carboxylic acid) was 1:1.

Prior to storage, the crude product obtained is doped with 1.1 g of methacrylic acid.

Molar Stoichiometry Prior to Storage: Glycidyl Methacrylate<Carboxylic Acid

| Storage stability at 30° C. | | Product | Start | 1 month | 3 months | 6 months | 8 months |
|---|---|---|---|---|---|---|---|
| Diester content [%] | min. 85.00 | 86.20% | 86.00% | 86.67% | 86.49% | 86.59% | 85.97% |
| Triester content [%] | max. 3.00 | 1.80% | 1.80% | 1.67% | 1.62% | 1.78% | 2.05% |
| Methacrylic acid [%] | | 0.42% | 0.65% | n.d. | n.d. | n.d. | n.d. |
| Glycidyl methacrylate [%] | | 0.72% | 0.72% | n.d. | n.d. | n.d. | n.d. |

| Storage stability at 50° C. | | Product | Start | 1 month | 3 months | 6 months | 8 months |
|---|---|---|---|---|---|---|---|
| Diester content [%] | min. 85.00 | 86.20% | 86.00% | 86.14% | 86.01% | 85.46% | 84.00% |
| Triester content [%] | max. 3.00 | 1.80% | 1.80% | 1.92% | 2.22% | 2.83% | 3.30% |
| Methacrylic acid [%] | | 0.42% | 0.65% | n.d. | n.d. | n.d. | n.d. |
| Glycidyl methacrylate [%] | | 0.72% | 0.72% | n.d. | n.d. | n.d. | n.d. |

Conclusion: The crude product prepared with a molar stoichiometry of 1:1 at the end of the reactant addition, but post-stabilized had a storage stability of 6 months, whereas the non-stabilized reference sample of Example 2 was not storage-stable.

Inventive Example 42

Post-Stabilization with a Carboxylic Acid Foreign to the System Prior to Storage Method according to Example 1, distinguished in that 179 g of methacrylic acid is used as carboxylic acid and at the end of the reactant addition the molar stoichiometry (glycidyl methacrylate:carboxylic acid) was 1:0.985.

Prior to storage, the crude product obtained is doped with 0.8 g of formic acid.

Molar Stoichiometry Prior to Storage: Glycidyl Methacrylate<Carboxylic Acid

| Storage stability at 30° C. | | Product | Start | 1 month | 3 months | 6 months | 8 months |
|---|---|---|---|---|---|---|---|
| Diester content [%] | min. 85.00 | 86.1% | 86.0% | 86.2% | 86.0% | 86.1% | 85.5% |
| Triester content [%] | max. 3.00 | 1.60% | 1.59% | 1.18% | 1.15% | 1.26% | 1.45% |
| Methacrylic acid [%] | | 0.40% | 0.40% | n.d. | n.d. | n.d. | n.d. |
| Glycidyl methacrylate [%] | | 0.78% | 0.78% | n.d. | n.d. | n.d. | n.d. |
| Formic acid [%] | | 0.00% | 0.16% | n.d. | n.d. | n.d. | n.d. |

| Storage stability at 50° C. | | Product | Start | 1 month | 3 months | 6 months | 8 months |
|---|---|---|---|---|---|---|---|
| Diester content [%] | min. 85.00 | 86.1% | 85.8% | 85.6% | 85.5% | 85.0% | 83.5% |
| Triester content [%] | max. 3.00 | 1.60% | 1.59% | 1.36% | 1.57% | 2.01% | 2.34% |
| Methacrylic acid [%] | | 0.40% | 0.71% | n.d. | n.d. | n.d. | n.d. |
| Glycidyl methacrylate [%] | | 0.78% | 0.78% | n.d. | n.d. | n.d. | n.d. |
| Formic acid [%] | | 0.00% | 0.16% | n.d. | n.d. | n.d. | n.d. |

Conclusion: The crude product prepared with a molar stoichiometry of 1:0.985 at the end of the reactant addition, but post-stabilized with formic acid as acid foreign to the system had a storage stability of 6 months, whereas the non-stabilized reference sample of Example 1 was not storage-stable.

Inventive Example 43

Post-Stabilization with Carboxylic Acid Foreign to the System Prior to Storage

Method according to Example 2, distinguished in that 181.7 g of methacrylic acid is used as carboxylic acid and at the end of the reactant addition the molar stoichiometry (glycidyl methacrylate:carboxylic acid) was 1:1.

Prior to storage, the crude product obtained is doped with 0.6 g of formic acid.

Molar Stoichiometry Prior to Storage: Glycidyl Methacrylate<Carboxylic Acid

| Storage stability at 30° C. | | Product | Start | 1 month | 3 months | 6 months | 8 months |
|---|---|---|---|---|---|---|---|
| Diester content [%] | min. 85.00 | 86.20% | 86.06% | 86.67% | 86.49% | 86.59% | 85.97% |
| Triester content [%] | max. 3.00 | 1.80% | 1.79% | 1.67% | 1.62% | 1.78% | 2.05% |
| Methacrylic acid [%] | | 0.42% | 0.65% | n.d. | n.d. | n.d. | n.d. |
| Glycidyl methacrylate [%] | | 0.72% | 0.72% | n.d. | n.d. | n.d. | n.d. |
| Formic acid [%] | | 0.00% | 0.12% | n.d. | n.d. | n.d. | n.d. |

| Storage stability at 50° C. | | Product | Start | 1 month | 3 months | 6 months | 8 months |
|---|---|---|---|---|---|---|---|
| Diester content [%] | min. 85.00 | 86.20% | 86.00% | 86.14% | 86.01% | 85.46% | 84.00% |
| Triester content [%] | max. 3.00 | 1.80% | 1.79% | 1.92% | 2.22% | 2.83% | 3.30% |

| Storage stability at 50° C. | Product | Start | 1 month | 3 months | 6 months | 8 months |
|---|---|---|---|---|---|---|
| Methacrylic acid [%] | 0.42% | 0.65% | n.d. | n.d. | n.d. | n.d. |
| Glycidyl methacrylate [%] | 0.72% | 0.72% | n.d. | n.d. | n.d. | n.d. |
| Formic acid [%] | 0.00% | 0.12% | n.d. | n.d. | n.d. | n.d. |

Conclusion: The product prepared with a molar stoichiometry of 1:1 at the end of the reactant addition, but the crude product post-stabilized with formic acid as acid foreign to the system had a storage stability of 6 months, whereas the non-stabilized reference sample of Example 2 was not storage-stable.

Inventive Example 44

Post-Stabilization with a Broensted Acid Prior to Storage

Method according to Example 1, distinguished in that 179 g of methacrylic acid is used as carboxylic acid and at the end of the reactant addition the molar stoichiometry (glycidyl methacrylate:carboxylic acid) was 1:0.985.

Prior to storage, the crude product obtained is doped with 0.55 g of phosphoric acid.

Molar Stoichiometry Prior to Storage: Glycidyl Methacrylate<Acid

| Storage stability at 30° C. | | Product | Start | 1 month | 3 months | 6 months | 8 months |
|---|---|---|---|---|---|---|---|
| Diester content [%] | min. 85.00 | 86.1% | 86.0% | 86.2% | 86.0% | 86.1% | 85.5% |
| Triester content [%] | max. 3.00 | 1.60% | 1.59% | 1.18% | 1.15% | 1.26% | 1.45% |
| Methacrylic acid [%] | | 0.40% | 0.40% | n.d. | n.d. | n.d. | n.d. |
| Glycidyl methacrylate [%] | | 0.78% | 0.78% | n.d. | n.d. | n.d. | n.d. |
| Phosphoric acid [%] | | 0.00% | 0.11% | n.d. | n.d. | n.d. | n.d. |

| Storage stability at 50° C. | | Product | Start | 1 month | 3 months | 6 months | 8 months |
|---|---|---|---|---|---|---|---|
| Diester content [%] | min. 85.00 | 86.1% | 86.0% | 85.6% | 85.5% | 85.0% | 83.5% |
| Triester content [%] | max. 3.00 | 1.60% | 1.59% | 1.36% | 1.57% | 2.01% | 2.34% |
| Methacrylic acid [%] | | 0.40% | 0.71% | n.d. | n.d. | n.d. | n.d. |
| Glycidyl methacrylate [%] | | 0.78% | 0.78% | n.d. | n.d. | n.d. | n.d. |
| Phosphoric acid [%] | | 0.00% | 0.11% | n.d. | n.d. | n.d. | n.d. |

Conclusion: The crude product prepared with a molar stoichiometry of 1:0.985 at the end of the reactant addition, but post-stabilized with phosphoric acid as inorganic acid foreign to the system had a storage stability of 6 months, whereas the non-stabilized reference sample of Example 1 was not storage-stable.

Inventive Example 45

Post-Stabilization with a Broensted Acid Prior to Storage

Method according to Example 2, distinguished in that 181.7 g of methacrylic acid is used as carboxylic acid and at the end of the reactant addition the molar stoichiometry (glycidyl methacrylate:carboxylic acid) was 1:1.

Prior to storage, the crude product obtained is doped with 0.25 g of phosphoric acid.

Molar Stoichiometry Prior to Storage: Glycidyl Methacrylate<Acid

| Storage stability at 30° C. | Product | Start | 1 month | 3 months | 6 months | 8 months |
|---|---|---|---|---|---|---|
| Diester content [%] | min. 85.00 | 86.20% | 86.06% | 86.67% | 86.49% | 86.59% | 85.97% |
| Triester content [%] | max. 3.00 | 1.80% | 1.79% | 1.67% | 1.62% | 1.78% | 2.05% |
| Methacrylic acid [%] | | 0.42% | 0.65% | n.d. | n.d. | n.d. | n.d. |
| Glycidyl methacrylate [%] | | 0.72% | 0.72% | n.d. | n.d. | n.d. | n.d. |
| Phosphoric acid [%] | | 0.00% | 0.05% | n.d. | n.d. | n.d. | n.d. |

| Storage stability at 50° C. | Product | Start | 1 month | 3 months | 6 months | 8 months |
|---|---|---|---|---|---|---|
| Diester content [%] | min. 85.00 | 86.20% | 86.06% | 86.14% | 86.01% | 85.46% | 84.00% |
| Triester content [%] | max. 3.00 | 1.80% | 1.79% | 1.92% | 2.22% | 2.83% | 3.30% |
| Methacrylic acid [%] | 0.42% | 0.65% | | n.d. | n.d. | n.d. | n.d. |
| Glycidyl methacrylate [%] | | 0.72% | 0.72% | n.d. | n.d. | n.d. | n.d. |
| Phosphoric acid [%] | | 0.00% | 0.05% | n.d. | n.d. | n.d. | n.d. |

Conclusion: The product prepared with a molar stoichiometry of 1:1 at the end of the reactant addition, but the crude product post-stabilized with phosphoric acid as inorganic acid foreign to the system had a storage stability of 6 months, whereas the non-stabilized reference sample of Example 2 was not storage-stable.

The invention claimed is:

1. A storage stable composition, comprising:
a) glycerol (meth)acrylate carboxylic esters selected from the group consisting of Formula (I) A, Formula (I) B and mixtures thereof, wherein, structurally, Formula (I) A and Formula (I) B are:

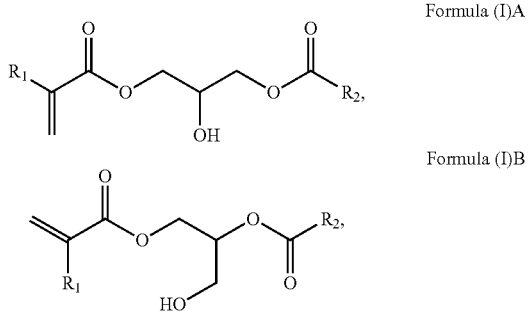

Formula (I)A

Formula (I)B and wherein:
$R_1$ is selected from the group consisting of H and CH3;
$R_2$ is selected from the group consisting of: hydrogen; a C1 to C30 aliphatic group optionally with a hydroxyl substituent; an aliphatic cyclic group with a C4 to C8 ring unsubstituted or substituted by N, S, O, or P; a C1 to C8 halogenated aliphatic group; an aromatic group having a ring with five or six carbons and optionally with a hydroxyl substituent; a heteroaromatic group substituted by N, S, O or P and having a ring with five or six carbons; and a C2 to C30 unsaturated aliphatic group;

b) carboxylic acids of formula (II):

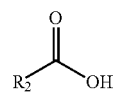

Formula (II)

wherein $R_2$ is hydrogen; a C1 to C30 aliphatic group optionally with a hydroxyl substituent; an aliphatic cyclic group with a C4 to C8 ring unsubstituted or substituted by N, S, O, or P; a C1 to C8 halogenated aliphatic group; an aromatic group having a ring with five or six carbons and optionally with a hydroxyl substituent; a heteroaromatic group substituted by N, S, O or P and having a ring with five or six carbons; or a C2 to C30 unsaturated aliphatic group; and
c) glycidyl (meth)acrylate;
d) optionally, Broensted acids;
wherein the sum total of the carboxylic acids of formula (II), and any Broensted acids that may be present, is in a molar ratio of from 1.01:1 to 2:1 relative to glycidyl (meth)acrylate, and this ratio is present after synthesis and before storage; and
when stored at 30° C. for 8 months, the composition maintains at least 85% by weight diester and no more than 3% by weight triester.

2. The storage stable composition of claim 1, wherein, the sum total of the carboxylic acids of formula (II) and Broensted acids are present in a molar ratio of from 1.02:1 to 1.5:1, relative to glycidyl (meth)acrylate and when stored at 50° C., storage stability lasts more than 6 months.

3. The storage stable composition of claim 1, wherein Broensted acids are not present.

4. The storage stable composition of claim 1, wherein Broensted acids are present.

5. The storage stable composition of claim 1, wherein the glycerol (meth)acrylate carboxylic esters are present as a mixture of esters of Formula (I) A and Formula (I) B.

6. The storage stable composition of claim 1, wherein R1 is methyl.

7. The storage stable composition of claim 1, wherein R2 is a C1 to C30 aliphatic group optionally with a hydroxyl substituent or a C2 to C30 unsaturated aliphatic group.

8. The storage stable composition of claim 1, wherein R2 is a C2 to C30 unsaturated aliphatic group.

9. The storage stable composition of claim 1, wherein R2 is an aliphatic cyclic group with a C4 to C8 ring unsubstituted or substituted by N, S, O, or P; a C1 to C8 halogenated aliphatic group; or a C2 to C30 unsaturated aliphatic group.

10. The storage stable composition of claim 1, wherein R2 is an aromatic group having a ring with five or six carbons and optionally with a hydroxyl substituent; a heteroaromatic group substituted by N, S, O, or P and having a ring with five or six carbons; or a C2 to C30 unsaturated aliphatic group.

11. The storage stable composition of claim 10, wherein R1 is methyl.

12. The storage stable composition of claim 11, wherein Broensted acids are not present.

13. The storage stable composition of claim 12, wherein Broensted acids are present.

14. The storage stable composition of claim 1, wherein R2 is isobutene.

15. The storage stable composition of claim 14, wherein R1 is methyl.

16. The storage stable composition of claim 15, wherein Broensted acids are not present.

* * * * *